United States Patent
Daye

(10) Patent No.: US 12,349,949 B2
(45) Date of Patent: *Jul. 8, 2025

(54) TIBIAL PLATEAU LEVELING OSTEOTOMY PLATE WITH OFFSET

(71) Applicant: Movora, LLC, Boston, MA (US)

(72) Inventor: Robert Mark Daye, Medina, OH (US)

(73) Assignee: Movora, LLC, Boston, MA (US)

( * ) Notice: Subject to any disclaimer, the term of this patent is extended or adjusted under 35 U.S.C. 154(b) by 500 days.

This patent is subject to a terminal disclaimer.

(21) Appl. No.: 17/213,114

(22) Filed: Mar. 25, 2021

(65) Prior Publication Data

US 2021/0212738 A1    Jul. 15, 2021

Related U.S. Application Data

(63) Continuation-in-part of application No. 17/026,931, filed on Sep. 21, 2020.

(60) Provisional application No. 62/903,110, filed on Sep. 20, 2019.

(51) Int. Cl.
| | |
|---|---|
| *A61B 17/80* | (2006.01) |
| *A61B 17/00* | (2006.01) |
| *A61B 17/15* | (2006.01) |
| *A61B 17/70* | (2006.01) |

(52) U.S. Cl.
CPC ............ *A61B 17/8061* (2013.01); *A61B 2017/00738* (2013.01); *A61B 17/157* (2013.01); *A61B 17/7059* (2013.01); *A61B 17/8014* (2013.01); *A61B 17/8052* (2013.01); *A61B 17/8057* (2013.01)

(58) Field of Classification Search
CPC . A61B 17/80; A61B 17/8014; A61B 17/8057; A61B 17/8061; A61B 17/808; A61B 17/157; A61B 17/7059; A61B 17/8052; A61B 17/8095; A61B 2017/00738
USPC ............ 606/280, 286, 88, 87, 902, 86 B, 70
See application file for complete search history.

(56) References Cited

U.S. PATENT DOCUMENTS

| | | | |
|---|---|---|---|
| 5,053,039 A | 10/1991 | Hofmann et al. | |
| 6,183,475 B1 * | 2/2001 | Lester ................ | A61B 17/8095 606/65 |
| D536,453 S | 2/2007 | Young et al. | |
| 7,722,653 B2 | 5/2010 | Young et al. | |
| 7,740,648 B2 | 6/2010 | Young et al. | |
| 7,905,883 B2 | 3/2011 | Bruecker et al. | |
| 8,080,010 B2 | 12/2011 | Schulz et al. | |

(Continued)

FOREIGN PATENT DOCUMENTS

| | | |
|---|---|---|
| CN | 106037914 A | 10/2016 |
| CN | 107928774 A | 4/2018 |
| EP | 3023068 A2 | 5/2016 |

OTHER PUBLICATIONS

Office Action mailed Apr. 27, 2023, issued in connection with U.S. Appl. No. 17/026,931 (18 pages).

(Continued)

*Primary Examiner* — Marcela I. Shirsat
(74) *Attorney, Agent, or Firm* — Klarquist Sparkman, LLP

(57) ABSTRACT

The device is a tibial plateau leveling osteotomy (TPLO) plate is used to stabilize a stifle joint in an animal in veterinary surgery after a torn cranial cruciate ligament. The TPLO plate has a proximal portion and a distal portion, connected by an offset portion.

20 Claims, 7 Drawing Sheets

(56) References Cited

U.S. PATENT DOCUMENTS

| | | | |
|---|---|---|---|
| 8,118,846 | B2 | 2/2012 | Leither et al. |
| 8,317,842 | B2 | 11/2012 | Graham et al. |
| 8,523,921 | B2 | 9/2013 | Horan et al. |
| 9,204,912 | B2 | 12/2015 | Price et al. |
| D765,844 | S | 9/2016 | DaCosta |
| D766,434 | S | 9/2016 | DaCosta |
| D767,136 | S | 9/2016 | Paik |
| D780,922 | S | 3/2017 | Dacosta |
| D780,923 | S | 3/2017 | DaCosta |
| D780,925 | S | 3/2017 | DaCosta |
| D785,178 | S | 4/2017 | Kohler et al. |
| D787,060 | S | 5/2017 | Kohler et al. |
| D812,757 | S | 3/2018 | Barmes et al. |
| 10,245,088 | B2 | 4/2019 | Dayton et al. |
| 10,299,841 | B2 | 5/2019 | Dunlop et al. |
| D874,003 | S | 1/2020 | DaCosta et al. |
| D874,004 | S | 1/2020 | DaCosta et al. |
| D874,650 | S | 2/2020 | Horan et al. |
| 10,786,290 | B2 | 9/2020 | Horan et al. |
| 10,905,479 | B2 | 2/2021 | Horan et al. |
| 11,026,728 | B2 | 6/2021 | Horan et al. |
| D945,623 | S | 3/2022 | Daye |
| D977,645 | S | 2/2023 | Mason et al. |
| D977,646 | S | 2/2023 | Mason et al. |
| D1,018,854 | S | 3/2024 | Daye |
| 2006/0089648 | A1 | 4/2006 | Masini |
| 2006/0149275 | A1 | 7/2006 | Cadmus |
| 2007/0233106 | A1* | 10/2007 | Horan ............... A61B 17/8061 606/282 |
| 2008/0039851 | A1 | 2/2008 | Schulz et al. |
| 2009/0024172 | A1 | 1/2009 | Pizzicara |
| 2010/0030276 | A1* | 2/2010 | Huebner ............ A61B 17/8061 606/280 |
| 2012/0265254 | A1* | 10/2012 | Horan ............... A61B 17/8061 606/289 |
| 2013/0338781 | A1 | 12/2013 | Bordeaux et al. |
| 2014/0180343 | A1 | 6/2014 | Gaudin |
| 2016/0128745 | A1* | 5/2016 | Sidebotham ....... A61B 17/8014 606/281 |
| 2016/0135858 | A1* | 5/2016 | Dacosta ............. A61B 17/808 606/280 |
| 2016/0310184 | A1* | 10/2016 | Kazanovicz ....... A61B 17/1728 |
| 2017/0007304 | A1* | 1/2017 | Kuroda ............. A61B 17/8061 |
| 2018/0325568 | A1* | 11/2018 | Wotton ............. A61B 17/8052 |
| 2019/0069937 | A1 | 3/2019 | Kuroda et al. |
| 2019/0274743 | A1 | 9/2019 | Dunlop et al. |
| 2021/0085380 | A1* | 3/2021 | Daye ................. A61B 17/8061 |
| 2021/0298806 | A2 | 9/2021 | Daye |
| 2021/0361331 | A1* | 11/2021 | Daye .................. A61B 17/808 |

OTHER PUBLICATIONS

Applicant-Initiated Inteview Summary mailed Nov. 17, 2022, issued in connection with U.S. Appl. No. 17/026,931 (3 pages).

Notice of Allowance dated Sep. 14, 2021, issued in connection with U.S. Appl. No. 29/771,085 (6 pages).

Office Action mailed Oct. 6, 2021, issued in connection with U.S. Appl. No. 17/026,931 (11 pages).

Applicant-Initiated Inteview Summary mailed Jun. 21, 2022, issued in connection with U.S. Appl. No. 17/026,931 (3 pages).

Declaration of Alex Khowaylo dated Oct. 20, 2022, attaching image of Cloverleaf Plate with Parallel Screws, a product that was availble prior to Sep. 20, 2019 (2 pages).

Office Action mailed Oct. 21, 2022, issued in connection with U.S. Appl. No. 17/026,931 (16 pages).

Office Action mailed Apr. 27, 2022, issued in connection with U.S. Appl. No. 17/026,931 (16 pages).

International Search Report of the International Searching Authority mailed on Jun. 16, 2022, issued in connection with International Application No. PCT/US2022/22012 (3 pages).

Written Opinion of the International Searching Authority mailed on Jun. 16, 2022, issued in connection with International Application No. PCT/US2022/22012 (8 pages).

International Search Report of the International Searching Authority mailed on Dec. 2, 2020, issued in connection with International Application No. PCT/US2020/51769 (3 pages).

Written Opinion of the International Searching Authority mailed on Dec. 2, 2020, issued in connection with International Application No. PCT/US2020/51769 (5 pages).

Notice of Allowance dated Nov. 2, 2021, issued in connection with U.S. Appl. No. 29/771,085 (7 pages).

International Preliminary Report on Patentability of the International Searching Authority mailed on Feb. 17, 2022, issued in connection with International Application No. PCT/US2020/51769 (14 pages).

Extended European Search Report dated Sep. 26, 2023, issued by the European Patent Office in connection with European Patent Application No. 20866115.7 (11 pages).

Office Action mailed Oct. 10, 2023, issued in connection with U.S. Appl. No. 17/393,616 (17 pages).

Notice of Allowance mailed Oct. 16, 2023, issued in connection with U.S. Appl. No. 29/829,907 (7 pages).

Office Action dated Nov. 20, 2023, issued by the Canadian Patent Office in connection with Canadian Patent Application No. 3,155,188 (4 pages).

Office Action mailed Jun. 11, 2024, issued in connection with U.S. Appl. No. 17/393,616 (12 pages).

Office Action issued in U.S. Appl. No. 17/026,931 on Jul. 10, 2024 (12 pages).

Extended European Search Report issued in European Application No. 22776751.4 by the European Patent Office on Mar. 24, 2025 (13 pages).

\* cited by examiner

TIBIAL PLATEAU LEVELING OSTEOTOMY PLATE WITH OFFSET

CROSS-REFERENCE TO RELATED APPLICATIONS

This application is a continuation-in-part of U.S. patent application Ser. No. 17/026,931, filed on Sep. 21, 2020 which claims the priority of U.S. Provisional Application Ser. No. 62/903,110, filed on Sep. 20, 2019, the contents of both of which are hereby incorporated by reference in its entirety and for all purposes.

BACKGROUND

Technical Field

The present disclosure relates to a tibial plateau leveling osteotomy plate (TPLO) with an offset, typically for use in veterinary surgery, with an animal, such as, but not limited to, a canine, a feline, or other quadruped animal species, both domestic and exotic.

Related Art

A tibial plateau leveling osteotomy (TPLO) plate is used in veterinary surgery to stabilize a stifle joint in an animal after a torn cranial cruciate ligament.

Current TPLO plates, when applied at an angle in a plane deviating from parallel to the long axis of the tibia, often result in abnormal angulation of the plate and screws, with the ensuing risk that a fixed angle screw could engage or enter structures such as joints, bones, or soft-tissue. Where the tibial plateau is translated during TPLO and the plate becomes offset from the bone surface, there can be increased bending stress placed on the screws, leading to cyclical loading to failure at far fewer cycles. Variations of anatomy, such as a mediolateral flared "trumpet-like" proximal tibia, can also lead to similar issues of plate offset from bone surface and angulation, even if the tibial plateau is rotated (leveled) without intentionally or unintentionally inducing translation in the mediolateral plane. Due to this unusual anatomy, an out-of-parallel plate application can result using the standard angle-stable TPLO plate.

SUMMARY

The present disclosure relates to a tibial plateau leveling osteotomy (TPLO) plate with offset. The TPLO plate with offset includes distal portion, an offset portion, and a proximal portion. The distal portion includes attachment apertures to secure the TPLO plate with offset to the body of the tibia. The proximal portion includes attachment apertures to secure the TPLO plate to an upper portion of a tibia or the osteotomized section of a tibia. The offset portion connects the proximal portion and the distal portion in an offset relation. The offset portion, or step or jog can be at 90° (i.e., perpendicular) or less than 90° with respect to both the distal portion and the proximal portion, such that the distal portion and the proximal portion are in parallel planes offset from each other. However, a section of the proximal portion may be twisted, rotated or inclined with respect to the plane of the remaining section of the proximal portion.

The TPLO plate typically allows mediolateral translation of the tibial plateau segment during TPLO and further typically allows the concurrent treatment of cranial cruciate ligament rupture and medial patella luxation. The TPLO plate is typically adapted to patients with trumpet-shaped or markedly flared proximal tibial anatomy or to patients with profound medial buttress (without necessitating extensive buttress elevation). The TPLO plate further is typically designed to facilitate TPLO plate placement parallel to the tibial long-axis and TPLO screw placement parallel to the joint surface. By providing multiple plates with different offsets, the surgeon is allowed to choose the preferred tibial plateau (tuberosity) translation or adapt to variable anatomy.

BRIEF DESCRIPTION OF THE DRAWINGS

The foregoing features will be apparent from the following Detailed Description, taken in connection with the accompanying drawings, in which.

DETAILED DESCRIPTION

The present disclosure relates to a tibial plateau leveling osteotomy (TPLO) plate with offset for a tibial plateau leveling osteotomy. The offset allows for translation of the osteotomized segment medially or laterally for alignment of the tibia, patella and quadriceps. This plate can be used for an apparatus in veterinary surgery for orthopedic surgical translation of an osteotomized segment in canines, felines, and other quadruped animal species, both domestic and exotic. The plate can be used to repair a torn cranial cruciate ligament while concurrently repairing a chronic pre-existing patella luxation.

The TPLO plate with offset allows translation of a proximal tibial segment while maintaining plate alignment parallel to a tibial long axis and screw alignment parallel a joint surface to minimize the risk of unacceptable screw impingement. Moreover, the apertures in the proximal tibial segment as well as those in the distal segment, for receiving locking screws or similar attachment elements, are perpendicular to the distal segment, notwithstanding the orientation of the proximal tibial element with respect to the distal element. This allows the locking screws in both the proximal tibial segment and the distal segment to remain perpendicular to the distal element and parallel to each other. The TPLO with offset minimizes plate-to-bone distance to minimize a risk of screw failure, and allows a surgeon to adapt to abnormal anatomy while maintaining a plate parallel to the tibial long axis to reduce risk of complications. Further, this offset, along with the orientation of the apertures in the proximal tibial element, typically allows the TPLO plate to accommodate a canine bone end whereby fixation screws passing through the distal end engage a length of the canine tibia and fixation screws passing through the proximal end to engage the bone in the cut freed proximal tibial section of the canine without extending into the stifle joint of the canine. The size, length or extent of the offset can vary according to the application (such as the size of the canine or the position and/or extent of the injury). The present disclosure relates to a tibial plateau leveling osteotomy (TPLO) plate with an offset. The TPLO plate with offset includes distal portion, an offset portion, and a proximate portion. The distal portion includes attachment apertures to secure the TPLO plate with offset to the body of the tibia. The proximal portion includes attachment apertures to secure the TPLO plate to an upper portion of a tibia or the osteotomized section of a tibia. The offset portion connects the proximal portion and the distal portion in an offset relation. The offset portion can be at 90° with respect to both the distal portion and the proximal portion such that the distal portion and the proximal portion are in parallel planes offset from each other. The length of the offset portion can be varied.

Figure 1:
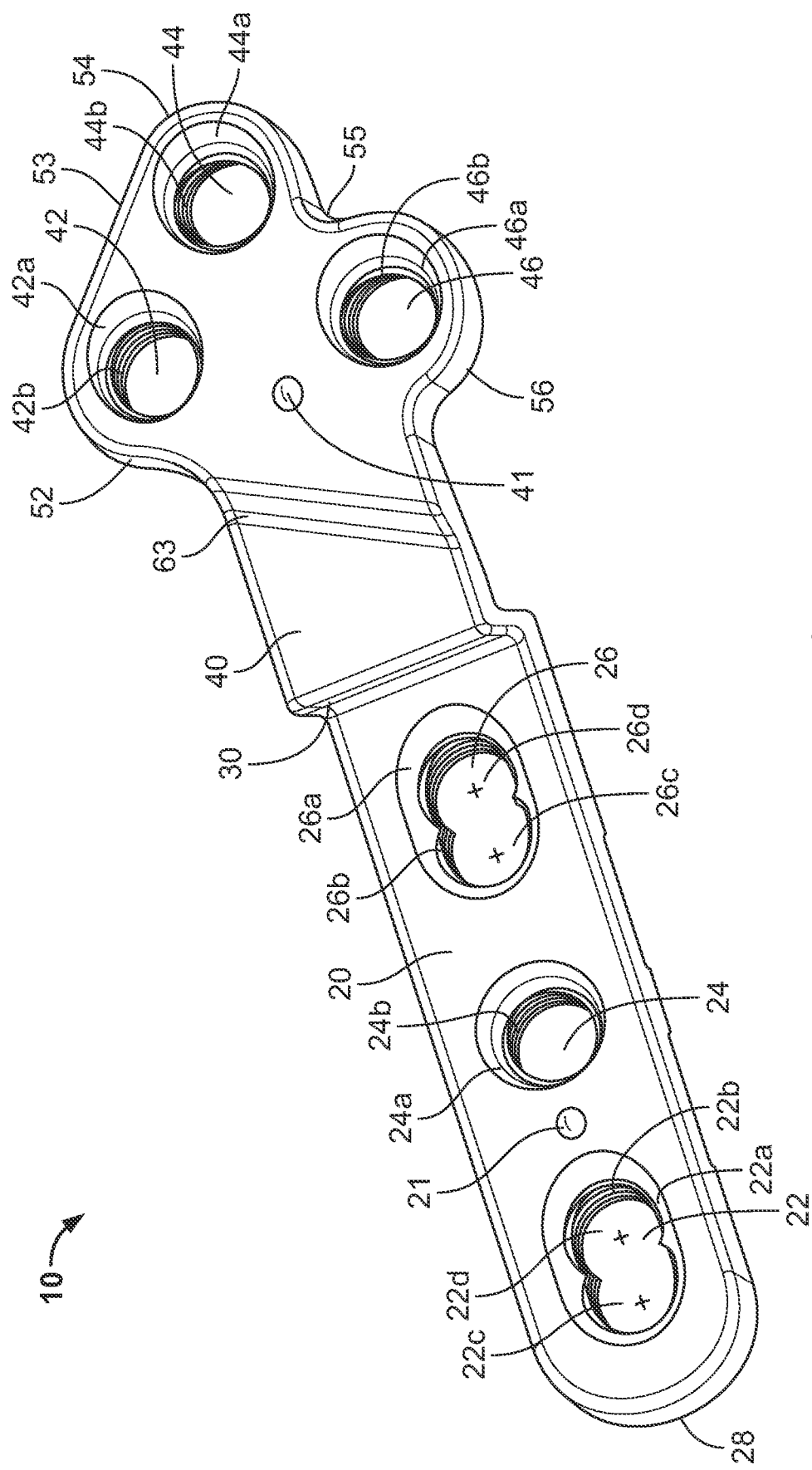
FIG. 1 is a perspective view of a tibial plateau leveling osteotomy plate with offset apparatus.
Figure 2:
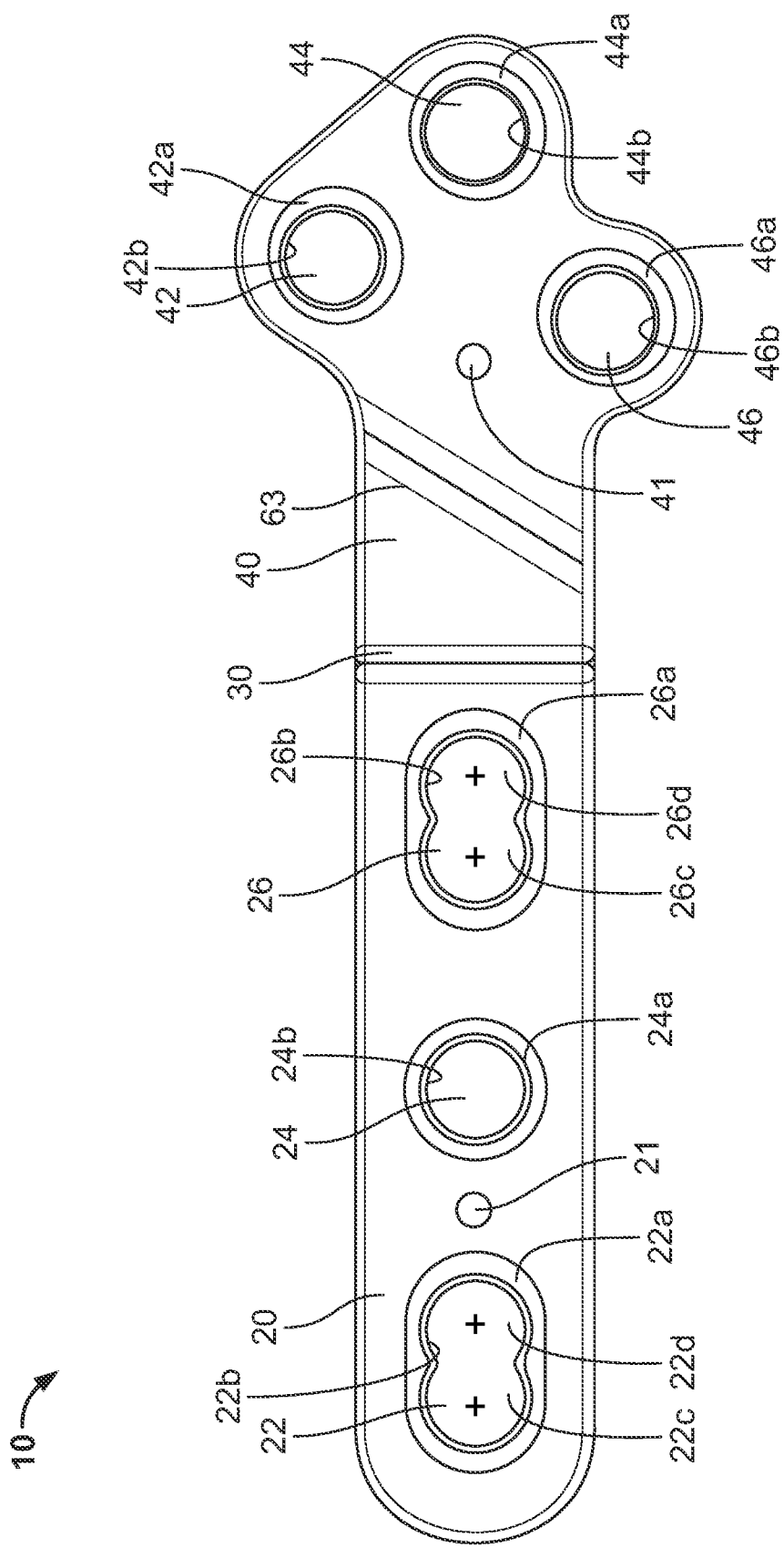
FIG. 2 is a top view of the apparatus shown in FIG. 1.
Figure 3:
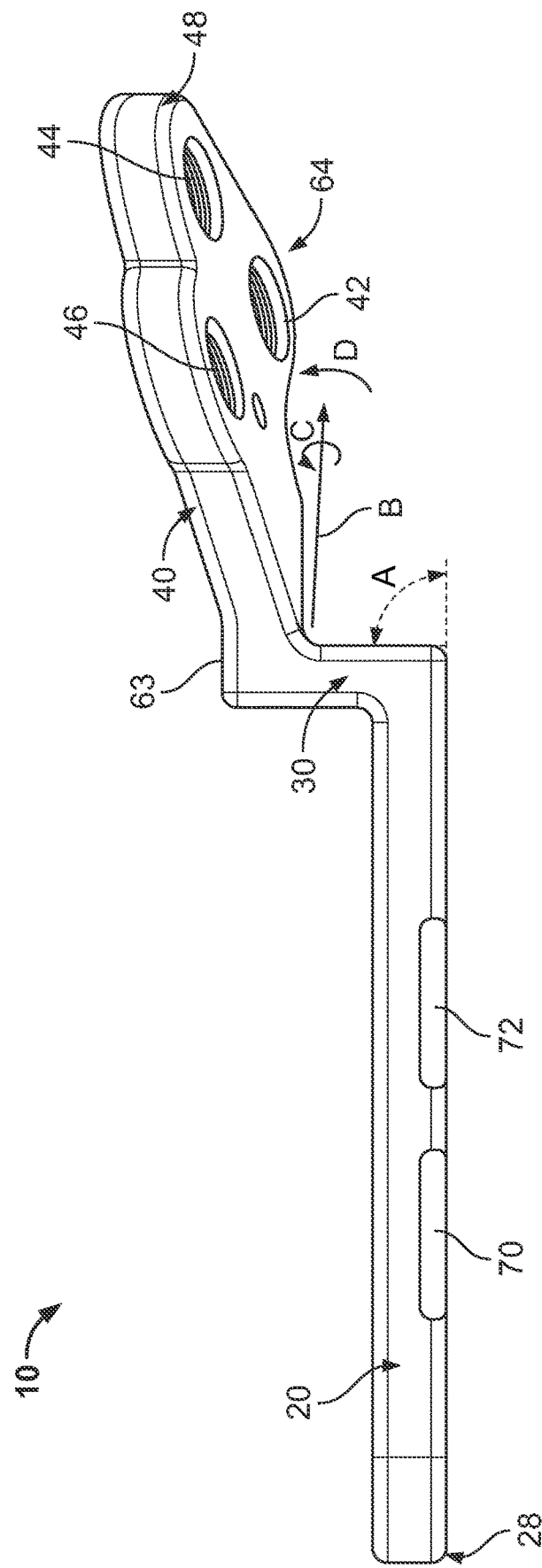
FIG. 3 is a side view of the apparatus shown in FIG. 1.

Referring now to the drawings in detail wherein like numerals refer to like elements throughout the several views, one see that FIGS. 1-3 show the TPLO plate with offset 10, indicated generally at 10. Specifically, FIG. 1 shows a perspective view, FIG. 2 shows a top view, and FIG. 3 shows a side view of the TPLO plate with offset 10. The TPLO plate with offset 10 comprises three portions: a distal portion 20, an offset portion 30, and a proximal portion 40.

The distal portion 20 includes one or more dual attachment apertures such as the illustrated dual-attachment apertures 22, 26. A one single attachment aperture 24 can also be included to secure the plate 10 to the body of the tibia. Apertures 22, 24, 26 include respective chamfered entrances 22a, 24a, 26a to capture an attachment device (see elements 200, FIGS. 4 and 6), and can have threaded portions 22b, 24b, and 26b for locking/threaded fixation hardware. Furthermore, dual attachment apertures 22, 26 are formed with two axes of rotation, offset from one another, 22c, 22d and 24c, 24d, respectively, each axis of which can have threaded portions. A pilot aperture 21, illustrated as configured as a hemispherical blind aperture, can be used for preliminary attachment. Any suitable type of attachment aperture can be used such as a single position aperture 24 or multiple position apertures 22 and 26. The apertures can be locking, as shown, with threading at lower portions thereof, or non-locking. The apertures can also be compression apertures. The attachment apertures 22, 24, 26 can be positioned linearly along a center or longitudinal axis of the distal portion 20 for proper attachment to a bone. However, the attachment apertures 22, 24, 26 can also be offset from the center axis of the distal portion 20 if desired. An end 28 of the distal portion 20 can be contoured to be elevated away from the bone of the distal tibia so as not to impede tibial soft tissues. For example, a clearance of 1-2 mm may be provided.

The proximal portion 40 includes attachment apertures 42, 44, 46, formed along the edge of proximal portion in a semi-circular configuration, which are used to secure the proximal portion 40 of the plate 10 to an upper portion of a bone, such as an osteotomized section of a tibia. Similar to attachment apertures 22, 24, 26, attachment apertures 42, 44, 46 include respective chamfered entrances 42a, 44a, 46a to capture an attachment device (see elements 200, FIGS. 4 and 6), and can have threaded portions 42b, 44b, and 46b for locking/threaded fixation hardware. A pilot aperture 41, illustrated as configured as a hemispherical blind aperture, can be used for preliminary attachment.

The apertures 42, 44, 46 of proximal portion 40 are typically oriented so as to be perpendicular to distal portion 20, even though, in some embodiments, the proximal portion 40 may be twisted, rotated, inclined or in some orientation other than parallel with the distal portion 20.

The proximal portion 40 can take on any suitable shape, such as linear, triangular, etc. As shown in the Figures, the proximal portion 40 could have a general triangular shape with first and second bulges 52 and 56 corresponding to attachment apertures 42 and 46, a generally straight edge 53, leading to a curved edge 54, around attachment aperture 44, and an edge 55 with a scalloped indentation between attachment apertures 44 and 46.

The attachment apertures 42, 44, 46 can be positioned in any location on the proximal portion 40 for proper attachment to an osteotomized segment of a bone. For example, attachment aperture 44 can be positioned at the apex of the plate 10 with its center being at a center plane running the length of the plate 10, attachment aperture 42 can be positioned towards the offset portion, flanking attachment aperture 44. An end 48 of the proximal portion 40 can be contoured to be elevated away from the bone of the distal tibia so as not to impede tibial soft tissues. For example, a clearance of 1-2 mm can be provided. Each attachment aperture 42, 44, 46 can comprise a fully or partially rounded exterior surface. It should be understood that the proximal portion 40 can contain any number of attachment apertures, such as two or more.

Each of the attachment apertures 22, 24, 26, 42, 44, 46 can be designed to receive a fastener, such as a bolt, a screw, or any other applicable fastening device (see element 200, FIGS. 4 and 6) Accordingly, these apertures can be threaded, tapered, rounded, etc. In the case of the dual attachment apertures 22, 26, these apertures can have multiple locations (e.g., apertures) for receiving a fastener, such as a screw. Each of the attachment apertures 22, 24, 26, 42, 44, 46 can be aligned in parallel to each other and extend through the front and back of generally planar faces. The diameter of the attachment apertures 22, 24, 26, 42, 44, 46 (including each dual aperture within attachment apertures 22, 26) can vary such that they can accept appropriate sized screw, or other fastener. For example, the attachment apertures 22, 24, 26, 42, 44, 46 could be 3.5 mm in diameter, to allow for the placement of a 3.5 mm cortical bone screw. These apertures can be sized to have a sufficient diameter such that the head of the screw, such as a 3.5 mm cortical screw, fits flush with the distal and proximal portions 20 and 40. Other sized bone screws, such as 2.0 mm, 2.7 mm, or 3.5 mm cortical bone screws can also be used, and the apertures could be sized accordingly to the given application.

As previously described, the apertures 42, 44, 46 of proximal portion 40 are aligned so as to be perpendicular with distal portion 20. This allows for the locking screws 200 (or similar attachment devices) engaged within apertures 42, 44, 46 to be parallel to each other and to be perpendicular to distal portion 20. Likewise, apertures 22, 24, 26 in distal portion 20 are oriented perpendicular to distal portion 20. This further provides that the locking screws 200 passing through apertures 42, 44, 46 of proximal portion are parallel with each other as well as parallel with the locking screws 200 passing through apertures 22, 24, 26 of distal portion 20. This orientation of the locking screws 200, along with the offset 30, typically allows the plate 10 to accommodate a canine bone end whereby fixation screws passing through the distal end engage a length of the canine tibia and locking screws 200 passing through the proximal end to engage the bone in the free tibial section of the canine without extending into the joint of the canine.

As shown in the Figures, the apertures 22, 24, 26, 42, 44, 46 can have a round or oblong profile to act as compression type holes. The overlapping holes include angled surfaces that create a compression effect as the TPLO plate 10 is attached to the bone 100, such that while the plate 10 is connected to a bone 100 via screws 200 mounted through the apertures a compressive force is imparted to the bone sections which causes the bone sections to move towards the center of the plate 10.

The apertures 22, 24, 26, 42, 44, 46 are shown with locking screw holes are threaded and designed to work with different designs of locking screws 200. Locking screws 200 thread into the plate 10 as well as into the bone 100.

The offset portion 30 links the distal portion 20 and the proximal portion 40 such that the proximal portion 40 is situated on a plane offset from the distal portion 20 but generally parallel thereto. The offset portion 30 can be oriented at angle A of 90° with respect to the distal and proximal portions 20 and 40, and this angle can be varied if desired. Accordingly, there is a first angle between the distal portion 20 and the offset portion 30, and a second angle between the offset portion 30 and the proximal portion 40. The offset portion 30 is generally perpendicular to the distal and proximal portions 20 and 40. The angle of the offset portion 30 could be less than perpendicular to facilitate manufacturing by stamping. The length of the offset portion 30 can be varied as suitable to the given application.

Different offsets can be used for different sized implants intended for various sized animals, and can be scaled in accordance to the average needs of a patient group. For example, a 3.5 mm plate can be designed with different offsets to allow for a range of accommodations. Any amount of offset could be engineered into the TPLO plate 10, such as a range of, for example, between 3 mm and 10 mm or more or less. Additionally, the proximal portion 40 may optionally include a bend 63 thereby causing an angle or curvature 64 (see FIG. 3), where the proximal portion 40 has a twist or a bend 63 to better attach to a osteotomized section of bone and further causing a portion of the proximal portion 40 to be on a plane which is twisted, rotated or inclined with respect to the plane of the remaining portion of the proximal portion 40. This twist, rotation or inclination is illustrated by a rotation C about axis B, or an inclination of axis B as indicated by arrow D in FIG. 3. As such, the proximal portion can be angled or turned about a long axis of the plate 10 so that a contact face of the proximal portion 40 is at an angle with respect to a contact face of the distal portion 20. Typically, however, the portion of proximal portion 40 immediately adjacent to offset portion 30 is in a plane parallel with that of distal portion 20. Other embodiments may include a proximal portion 40 which is entirely in a plane parallel to that of distal portion 20.

As further illustrated in FIG. 3, the lower surface of distal portion 20 can include undercuts 70, 72 (some embodiments includes similar undercuts on the opposite unillustrated side of distal portion 20).

The TPLO plate 10 with offset can be formed from any number of biocompatible, implantable materials. These materials include, but are not limited to, 316 stainless steel, titanium, or ultra-high-molecular-weight polyethylene. Exposed edges of the plate 10 can be rounded and smooth. The length of the plate 10 can vary with the size of the patient. Similarly, the thickness of the plate 10 can vary with the size of the patient.

Figure 4:
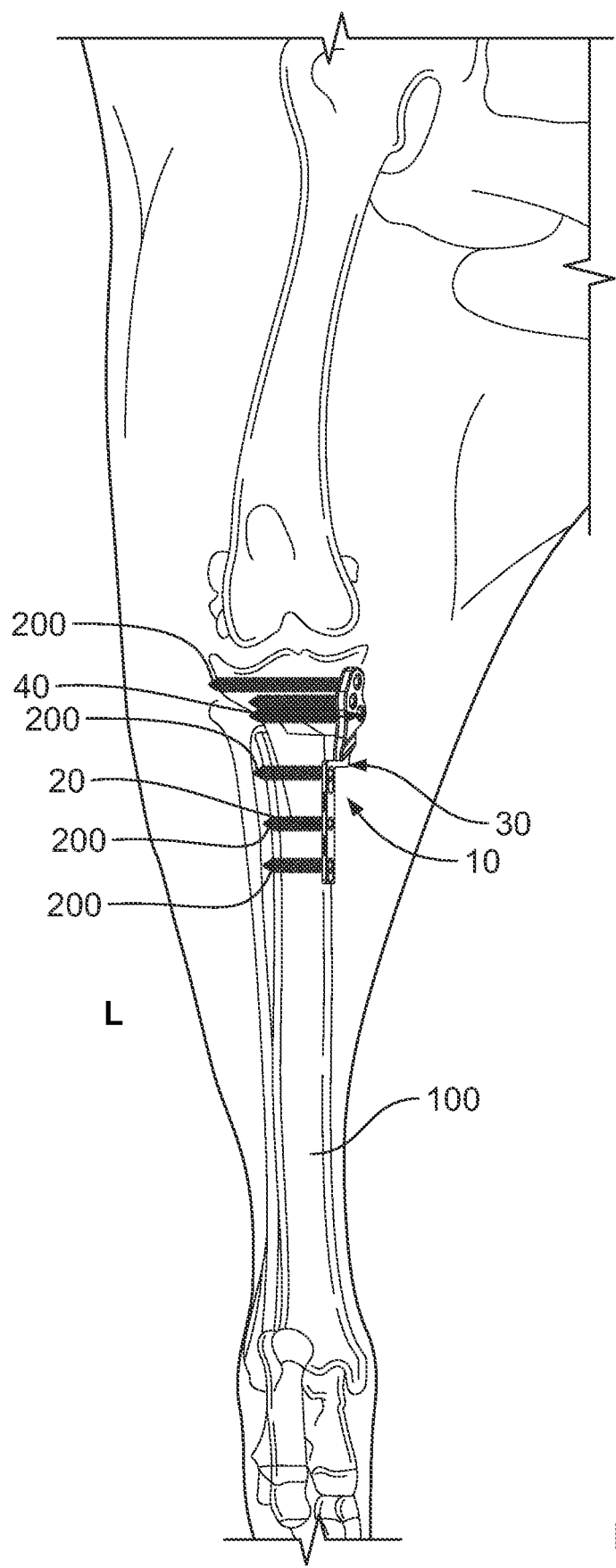
FIG. 4 illustrates a side view of the apparatus of FIG. 1 implanted in a canine's leg.
Figure 5:
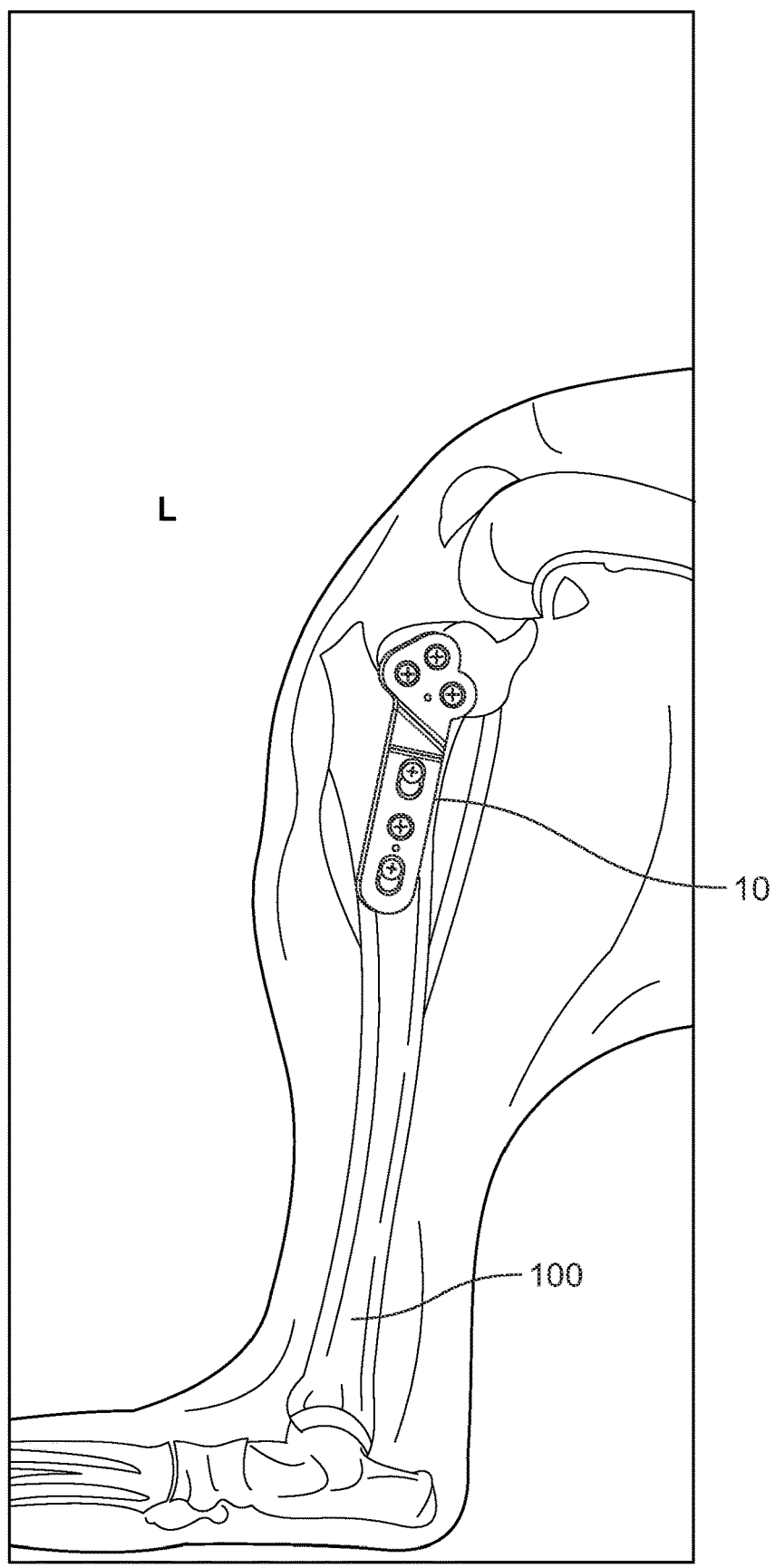
FIG. 5 illustrates a top view of the apparatus of FIG. 1 implanted in the canine's leg.
Figure 6:
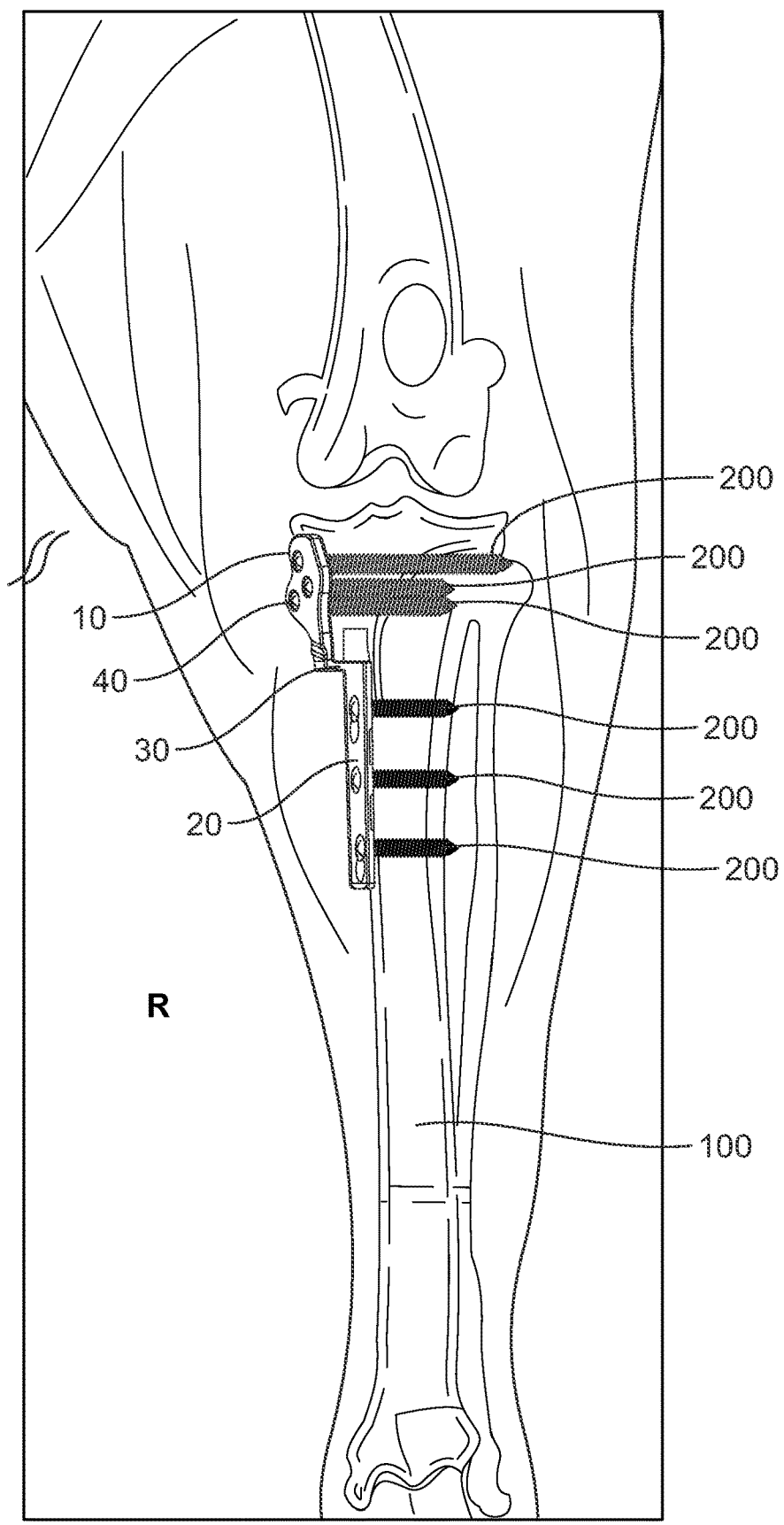
FIG. 6 illustrates a further side view of the apparatus of FIG. 1 implanted in a canine's leg.

FIGS. 4, 5 and 6 illustrate the TPLO plate with offset 10 affixed to a canine's leg bone 100 and attached by attachment elements 200. Specifically, FIGS. 4 and 6 illustrate a side view of the TPLO plate 10 with offset affixed to the canine's leg. The distal end 20 of the plate 10 is secured to the body of the canine's tibia. The proximal end 40 of the plate 10 is secured to an osteotomized section of the canine's tibia. FIG. 5 illustrates a top view of the TPLO plate with offset 10 affixed to the canine's leg.

Figure 7:
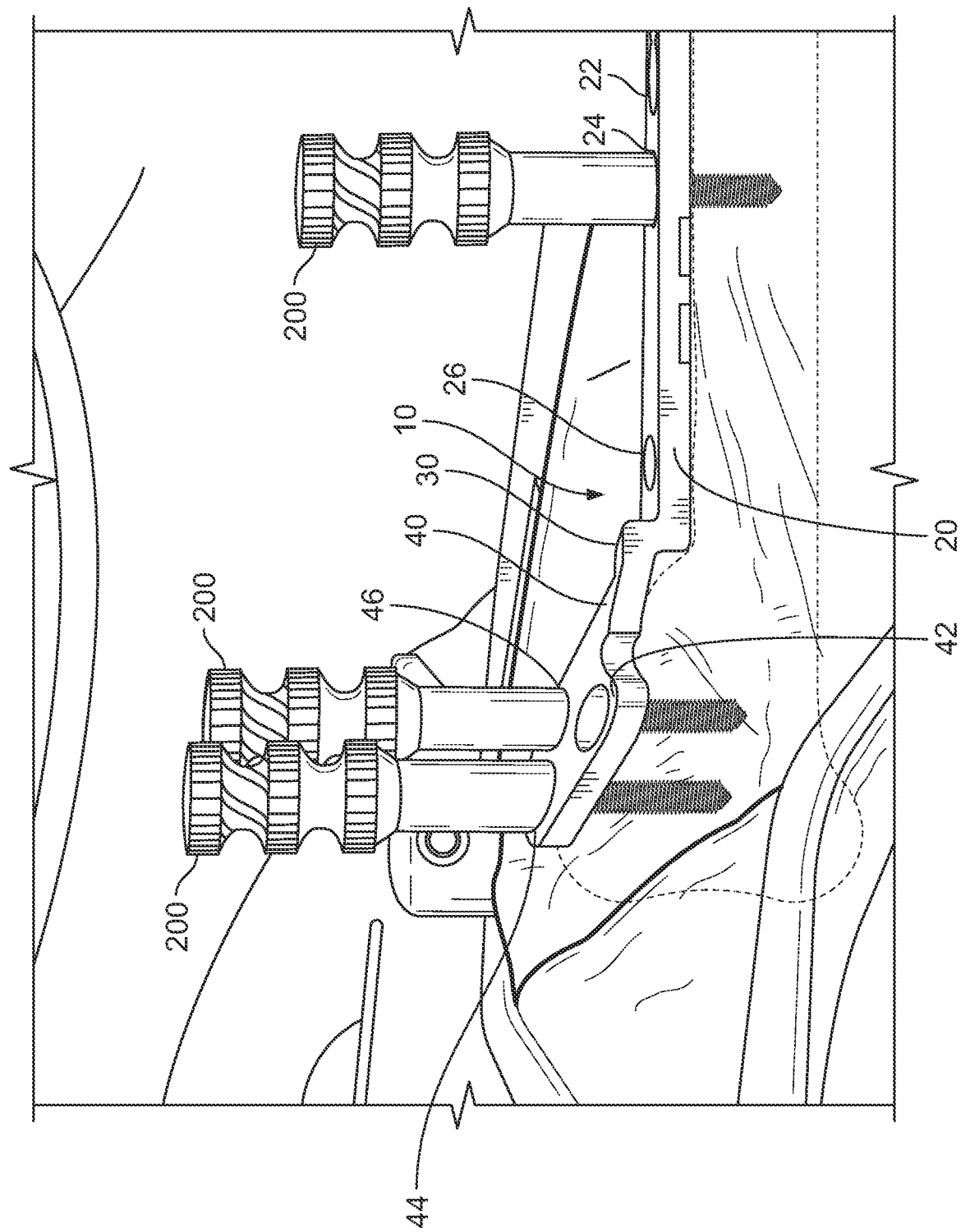
FIG. 7 illustrates a further view of the apparatus of FIG. 1 on a canine's leg.

FIG. 7 illustrates the TPLO plate with offset 10 on the tibia 100 of a canine. This illustrates the ease of application and the parallel configuration of apertures 22, 24, 26, 42, 44, 46 (as well as the locking screws 200 passing therethrough). In particular, the offset portion 30 typically allows the TPLO plate with offset 10 to accommodate a canine bone end thereby providing for the locking screws 200 to engage the bone in the freed proximal tibial section of the canine without unintentionally extending into the stifle joint. The size, length or extent of the offset portion 30 can vary according to the application (such as the size of the canine or the position and/or extent of the injury). As can be seen, the parallel nature of the fixation hardware is facilitated by angled apertures in the proximal head of the plate to the extent that the plate is twisted, rotated or inclined.

Having thus described the system and method in detail, it is to be understood that the foregoing description is not intended to limit the spirit or scope thereof. It will be understood that the embodiments of the present disclosure described herein are merely exemplary and that a person skilled in the art can make any variations and modification without departing from the spirit and scope of the disclosure. All such variations and modifications, including those discussed above, are intended to be included within the scope of the disclosure.

What is claimed is:

1. A tibial plateau leveling osteotomy plate, comprising:
   a proximal portion including a plurality of first attachment apertures;
   a distal portion including at least one second attachment aperture;
   the plurality of first attachment apertures and the at least one second attachment aperture all having central axes that are oriented perpendicular to the distal portion; and
   an offset portion joining the proximal portion to the distal portion, the offset portion comprising a step formed between the distal portion and the proximal portion such that the proximal portion is in a different plane from the distal portion, the proximal portion further comprising a bend proximal of the step such that a first portion of the proximal portion that is between the step and the bend is on a plane parallel to the distal portion, and a second portion of the proximal portion that is proximal of the bend is inclined upwardly relative to the distal portion;
   wherein the plate is configured such that attachment fixtures passing through the distal portion to enter a body of a tibia and attachment fixtures passing through the proximal portion to enter into a free tibial portion of the tibia are in parallel configuration.

2. The plate of claim 1 wherein the second portion of the proximal portion is on a different plane with respect to the plane of the first portion of the proximal portion.

3. The plate of claim 1 wherein the second portion of the proximal portion is on a plane which is rotated with respect to the plane of the first portion of the proximal portion.

4. The plate of claim 1 wherein the second portion of the proximal portion is on a plane which is rotated with respect to a long axis of the plate such that a lower contact face of the second portion is at an angle to a contact face of the distal portion.

5. The plate of claim 1 wherein the plurality of first attachment apertures is on the second portion of the proximal portion.

6. The plate of claim 5, wherein the first attachment apertures are arranged in a semi-circular configuration.

7. The plate of claim 6, wherein the at least one second attachment aperture is one of a plurality of second attachment apertures.

8. The plate of claim 7, wherein the second attachment apertures are arranged linearly along a longitudinal axis of the distal portion.

9. The plate of claim 8, wherein at least one of the first attachment apertures on the proximal portion is arranged in line with the plurality of second attachment apertures on the distal portion.

10. The plate of claim 9, wherein the linearly arranged second attachment apertures are flanked on either side by first attachment apertures on the proximal portion.

11. The plate of claim 10, wherein at least one of the plurality of second attachment apertures includes dual attachment apertures with two axes of rotation offset from each other.

12. The plate of claim 1 wherein the plate is adapted for surgical applications with canines, felines or quadruped animals.

13. The plate of claim 1 wherein the plate is made from a material chosen from the group consisting of 316 stainless steel, titanium, and ultra-high-molecular-weight polyethylene.

14. The plate of claim 1, wherein the at least one second attachment aperture is one of a plurality of second attachment apertures on the distal portion, and axes of the first attachment apertures of the proximal portion and axes of the second attachment apertures of the distal portion are all parallel to each other.

15. The plate of claim 1, wherein when viewed from the top, the step and the bend are at an angle to each other.

16. A tibial plateau leveling osteotomy plate, comprising:
a proximal portion including a plurality of first attachment apertures;
a distal portion including at least one second attachment aperture;
the plurality of first attachment apertures and the at least one second attachment aperture all having central axes that are oriented to be perpendicular to the distal portion; and
an offset portion joining the proximal portion to the distal portion, the offset portion comprising a step formed between the distal portion and the proximal portion such that the proximal portion is in a different plane from the distal portion, the proximal portion further comprising a bend proximal of the step, and wherein a first portion of the proximal portion that is between the step and the bend is on a plane parallel to the distal portion and a second portion of the proximal portion that is proximal of the bend is inclined upwardly relative to the distal portion;
wherein the plurality of first attachment apertures and the at least one second attachment aperture are configured to accommodate fixation hardware positioned so that the fixation hardware all extends parallel.

17. The plate of claim 16 wherein one or more of the plurality of first attachment apertures of the proximal portion are at an angle to the plate so that fixation hardware extending therethough is parallel with the fixation hardware extending through the distal portion.

18. The plate of claim 16 wherein the first and second attachment apertures are oriented so that the fixation hardware in the proximal portion is parallel to fixation hardware in the distal portion.

19. The plate of claim 16, wherein the at least one second attachment aperture is one of a plurality of second attachment apertures on the distal portion, and the plurality of first attachment apertures of the proximal portion and the plurality of second attachment apertures of the distal portion are all are configured to accommodate fixation hardware so that all the fixation hardware extends parallel.

20. The plate of claim 16, wherein when viewed from the top, the step and the bend are at an angle to each other.

* * * * *